(12) United States Patent
Wachendorff-Neumann et al.

(10) Patent No.: US 6,787,567 B2
(45) Date of Patent: Sep. 7, 2004

(54) FUNGICIDAL ACTIVE INGREDIENTS COMBINATIONS

(75) Inventors: Ulrike Wachendorff-Neumann, Neuwied (DE); Thomas Seitz, Langenfeld (DE); Herbert Gayer, Monheim (DE); Ulrich Heinemann, Leichlingen (DE); Bernd-Wieland Krüger, Bergisch Gladbach (DE); Wolfgang Krämer, Burscheid (DE); Lutz Assmann, Langenfeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/257,740

(22) PCT Filed: Apr. 9, 2001

(86) PCT No.: PCT/EP01/04042

§ 371 (c)(1),
(2), (4) Date: Oct. 16, 2002

(87) PCT Pub. No.: WO01/80641

PCT Pub. Date: Nov. 1, 2001

(65) Prior Publication Data

US 2003/0158151 A1 Aug. 21, 2003

(30) Foreign Application Priority Data

Apr. 20, 2000 (DE) .......................................... 100 19 758

(51) Int. Cl.$^7$ .......................... A01N 47/28; A61K 31/17
(52) U.S. Cl. ...................................... 514/588; 424/405
(58) Field of Search .................................. 514/588, 294; 424/405

(56) References Cited

U.S. PATENT DOCUMENTS

| | | | |
|---|---|---|---|
| 1,972,961 A | 9/1934 | Tisdale et al. ................. | 167/22 |
| 2,553,770 A | 5/1951 | Kittleson ....................... | 167/33 |
| 3,290,353 A | 12/1966 | Battershell et al. .......... | 260/465 |
| 3,513,241 A | 5/1970 | Hoyer et al. ................. | 424/300 |
| 3,745,170 A | 7/1973 | Fujinami et al. ....... | 260/326.5 S |
| 3,755,350 A | 8/1973 | Sauli ........................ | 260/309.5 |
| 3,823,240 A | 7/1974 | Sauli .......................... | 424/273 |
| 3,903,090 A | 9/1975 | Fujinami et al. ............. | 260/281 |
| 3,912,752 A | 10/1975 | Meiser et al. ........... | 260/308 R |
| 3,952,002 A | 4/1976 | Kramer et al. .......... | 260/308 R |
| 3,991,071 A | 11/1976 | Brookes et al. ............. | 260/309 |
| 4,009,278 A | 2/1977 | Fujinami et al. ............. | 424/274 |
| 4,048,318 A | 9/1977 | Meiser et al. ............... | 424/269 |

(List continued on next page.)

FOREIGN PATENT DOCUMENTS

| | | |
|---|---|---|
| CA | 2043733 | 12/1991 |
| DE | 195 28 651 | 2/1997 |
| WO | 96/23763 | 8/1996 |
| WO | 98/23155 | 6/1998 |
| WO | 98/47367 | 10/1998 |

OTHER PUBLICATIONS

Weeds, (month unavailable) 1967, pp. 20–22, "Calculating Synergistic and Antagonistic Responses of Herbicide Combinations" by S. R. Colby.
Pesticide Manual, 9th ed., (month unavailable) 1991, pp. 206–207, 3660 Cymoxanil.
Pesticide Manual, 9th ed., (month unavailable) 1991, p. 249, 4130 Dichlobenil.
Pesticide Manual, 9th ed., (month unavailable) 1991, p. 431–432, 6700 Folpet.
Pesticide Manual, 9th ed., (month unavailable) 1991, p. 443, 6780 Fosetyl.
Pesticide Manual, 9th ed., (month unavailable) 1991, p. 461, 6980 Guazatine.
Pesticide Manual, 9th ed., (month unavailable) 1991, pp. 461–462, 7010 Haloxyfop.
Pesticide Manual, 9th ed., (month unavailable) 1991, p. 461, 7242 Imidacloprid.
Pesticide Manual, 9th ed., (month unavailable) 1991, p. 529, 7760 Mancozeb.
Pesticide Manual, 9th ed., (month unavailable) 1991, pp. 531–532, 7770 Maneb.
Pesticide Manual, 9th ed., (month unavailable) 1991, pp. 554–555, 7990 Metalaxyl.
Pesticide Manual, 9th ed., (month unavailable) 1991, p. 827, 11740 Tolylfluanid.
Pesticide Manual, 9th ed., (month unavailable) 1991, p. 654, 9375 Penconazole.
Pesticide Manual, 9th ed., (month unavailable) 1991, p. 726, 10180 Propineb.
Pesticide Manual, 9th ed., (month unavailable) 1991, pp. 866–867, 12410 Zineb.
Pesticide Manual, 9th ed., (month unavailable) 1991, pp. 529–530, 7760 Mancozeb.

*Primary Examiner*—Alton N. Pryor
(74) *Attorney, Agent, or Firm*—Richard E.L. Henderson

(57) ABSTRACT

The invention relates to novel fungicidally active compound combinations of
(a) methoximinoacetamide derivatives of the general formula (I),

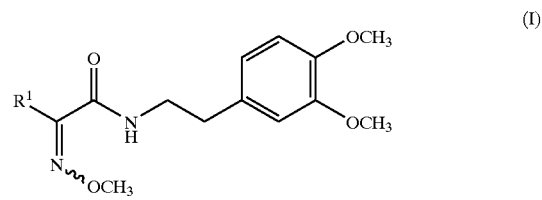

in which
R$^1$ represents unsubstituted or fluorine-, chlorine-, bromine-, methyl-, ethyl-, n- or i-propyl-, n-, i- or t-butyl-, methoxy-, ethoxy-, or phenoxy-substituted phenyl, 2-naphthyl, 1,2,3,4-tetrahydronaphthyl, indanyl, 2-benzofuranyl, 2-benzothienyl, 2-thienyl, or 2-furanyl, and
(b) the active compound groups (I) to (58) listed in the disclosure.

9 Claims, No Drawings

U.S. PATENT DOCUMENTS

| | | | |
|---|---|---|---|
| 4,079,062 A | 3/1978 | Van Reet et al. | 260/308 R |
| 4,147,791 A | 4/1979 | Meiser et al. | 424/269 |
| 4,154,945 A | 5/1979 | Brookes et al. | 548/341 |
| 4,160,838 A | 7/1979 | Van Reet et al. | 424/269 |
| 4,291,049 A | 9/1981 | Bosone et al. | 424/275 |
| 4,331,670 A | 5/1982 | Nishiyama et al. | 424/263 |
| 4,347,253 A | 8/1982 | Harr | 424/272 |
| 4,425,357 A | 1/1984 | Bosone et al. | 424/278 |
| 4,432,989 A | 2/1984 | Spencer | 424/273 R |
| 4,436,744 A | 3/1984 | Harr | 424/272 |
| 4,457,937 A | 7/1984 | Sandmeier et al. | 424/272 |
| 4,496,551 A | 1/1985 | Moberg | 514/63 |
| 4,510,136 A | 4/1985 | Moberg | 514/63 |
| 4,532,341 A | 7/1985 | Holmwood et al. | 549/559 |
| 4,608,385 A | 8/1986 | Noguchi et al. | 514/444 |
| 4,626,595 A | 12/1986 | Holmwood et al. | 549/559 |
| 4,664,696 A | 5/1987 | Schaub | 71/92 |
| 4,705,800 A | 11/1987 | Nyfeler et al. | 514/422 |
| 4,723,984 A | 2/1988 | Holmwood et al. | 71/76 |
| 4,780,551 A | 10/1988 | Nyfeler et al. | 549/422 |
| 4,789,672 A | 12/1988 | Holmwood et al. | 514/184 |
| 4,829,085 A | 5/1989 | Wenderoth et al. | 514/522 |
| 4,849,439 A | 7/1989 | Schaub | 514/383 |
| 4,851,405 A | 7/1989 | Kramer et al. | 514/212 |
| 4,871,390 A | 10/1989 | Holmwood et al. | 71/92 |
| 4,897,107 A | 1/1990 | Holmwood et al. | 71/92 |
| 4,904,298 A | 2/1990 | Holmwood et al. | 71/92 |
| 4,906,652 A | 3/1990 | Karbach et al. | 514/383 |
| 4,910,200 A | 3/1990 | Curtze et al. | 514/237.5 |
| 4,920,139 A | 4/1990 | Fujimoto | 514/383 |
| 4,925,840 A | 5/1990 | Nyfeler et al. | 514/228.2 |
| 4,931,560 A | 6/1990 | Hubele | 544/315 |
| 4,931,581 A | 6/1990 | Schurter et al. | 560/18 |
| 4,957,933 A | 9/1990 | Geffken et al. | 514/376 |
| 4,988,734 A | 1/1991 | Kraatz et al. | 514/624 |
| 4,992,438 A | 2/1991 | Ito et al. | 514/275 |
| 4,995,898 A | 2/1991 | Nasu et al. | 71/90 |
| 4,997,941 A | 3/1991 | Hubele | 544/332 |
| 5,021,581 A | 6/1991 | Clough et al. | 546/309 |
| 5,059,623 A | 10/1991 | Krüger et al. | 514/613 |
| 5,081,141 A | 1/1992 | Colle et al. | 514/383 |
| 5,087,635 A | 2/1992 | Shaber | 514/383 |
| RE33,989 E | 7/1992 | Wenderoth et al. | 514/522 |
| 5,145,843 A | 9/1992 | Arnold et al. | 514/63 |
| 5,153,200 A | 10/1992 | Hubele | 514/275 |
| 5,190,928 A | 3/1993 | Schurter et al. | 514/63 |
| 5,221,691 A | 6/1993 | Clough et al. | 514/619 |
| 5,223,523 A | 6/1993 | Adams, Jr. et al. | 514/376 |
| 5,240,940 A | 8/1993 | Arnold et al. | 514/312 |
| 5,264,440 A | 11/1993 | Clough et al. | 514/269 |
| 5,266,585 A | 11/1993 | Hubele et al. | 514/383 |
| 5,304,572 A | 4/1994 | Michelotti et al. | 514/514 |
| 5,330,995 A | 7/1994 | Eicken et al. | 514/355 |
| 5,334,607 A | 8/1994 | Sauter et al. | 514/378 |
| 5,342,837 A | 8/1994 | Clough et al. | 514/247 |
| 5,356,908 A | 10/1994 | Geffken et al. | 514/333 |
| 5,395,837 A | 3/1995 | Clough et al. | 514/269 |
| 5,407,902 A | 4/1995 | Oda et al. | 504/336 |
| 5,438,059 A | 8/1995 | Clough et al. | 514/256 |
| 5,453,531 A | 9/1995 | Seitz et al. | 560/29 |
| 5,468,747 A | 11/1995 | Clough et al. | 514/239.5 |
| 5,480,897 A | 1/1996 | Eicken et al. | 514/365 |
| 5,514,643 A | 5/1996 | Rew et al. | 504/266 |
| 5,523,311 A | 6/1996 | Schurter et al. | 548/361 |
| 5,556,988 A | 9/1996 | Eicken et al. | 548/374.1 |
| 5,589,493 A | 12/1996 | Eicken et al. | 514/355 |
| 5,637,729 A | 6/1997 | Lacroix et al. | 548/316.7 |
| 5,650,519 A | 7/1997 | Lacroix et al. | 548/316.7 |
| 5,789,430 A | 8/1998 | Jautelat et al. | 514/272.4 |
| 5,859,039 A | 1/1999 | Jautelat et al. | 514/384 |
| 5,869,517 A | 2/1999 | Müller et al. | 514/407 |
| 5,883,250 A | 3/1999 | Krüger et al. | 540/544 |
| 5,889,059 A | 3/1999 | Bayer et al. | 514/619 |
| 5,948,932 A | 9/1999 | Grote et al. | 558/422 |
| 5,981,581 A | 11/1999 | Bayer et al. | 514/522 |
| 6,002,016 A | 12/1999 | Lacroix et al. | 548/318.1 |
| 6,018,052 A | 1/2000 | Lacroix et al. | 548/318.1 |
| 6,020,354 A | 2/2000 | Assmann et al. | 514/380 |
| 6,037,378 A | 3/2000 | Grote et al. | 514/640 |
| 6,054,592 A | 4/2000 | Müller et al. | 548/371.1 |
| 6,100,263 A | 8/2000 | Bayer et al. | 514/241 |
| 6,103,717 A | 8/2000 | Heinemann et al. | 514/229.2 |
| 6,127,547 A | 10/2000 | Assmann et al. | 548/302.1 |
| 6,130,251 A | 10/2000 | Seitz et al. | 514/620 |
| 6,160,001 A | 12/2000 | Assmann et al. | 514/395 |
| 6,187,812 B1 | 2/2001 | Bayer et al. | 514/522 |
| 6,235,743 B1 | 5/2001 | Gayer et al. | 514/269 |
| 6,268,508 B1 | 7/2001 | Assmann et al. | 548/302.1 |
| 6,344,564 B1 | 2/2002 | Lacroix et al. | 548/318.1 |
| 6,359,133 B2 | 3/2002 | Gayer et al. | 544/319 |
| 6,387,939 B1 | 5/2002 | Assmann et al. | 514/395 |
| 6,407,233 B1 | 6/2002 | Heinemann et al. | 544/65 |
| RE37,873 E | 10/2002 | Bayer et al. | 514/522 |
| 2001/0018442 A1 | 8/2001 | Gayer et al. | 514/269 |
| 2003/0027842 A1 | 2/2003 | Assmann et al. | 514/322 |

FUNGICIDAL ACTIVE INGREDIENTS COMBINATIONS

The present relation relates to novel active compound combinations which consist of known methoximinoacetamide derivatives and further known fungicidally active compounds, and which are highly suitable for controlling phytopathogenenic fungi.

It is already known that alkoximinoacetamide derivatives have fungicidal properteis (cf. WO 96/23763). The activity of these compounds is good; however, at low application rates it is in some cases not satisfactory.

Furthermore, it is already known that a large number of triazole derivatives, aniline derivatives, dicarboximides and other heterocycles can be employed for controlling fungi (cf. EP-A 0 040 345, DE-A 22 01 063, DE-A 23 24 010, Pesticide Manual, 9th. Edition (1991), pages 249 and 827, EP-A 0 382 375 and EP-A 0 515 901). Likewise, the activity of these compounds is not always satisfactory at low application rates.

Finally, it is also known that 1-[(6-chloro-3-pyridinyl)-methyl]-N-nitro-2-imidazo-lidinimine can be used for controlling animal pests such as insects (cf. Pesticide Manual, 9th. Edition (1991), page 491). However, fungicidal properties have hitherto not been described for this compound.

Furthermore, it is already known that 1-(3,5-dimethyl-isoxazole-4-sulphonyl)-2-chloro-6,6-difluoro-[1,3]-dioxolo-[4,5f]-benzimidazole has fungicidal properties (cf. WO 97-06171).

Furthermore, it is already known that substituted aza-dioxacycloalkenes have fungicidal properties (cf. EP-B-712 396).

Finally, it is also known that substituted halogenopyrimidines have fungicidal properties (cf. DE-AI-196 46 407, EP-B-712 396).

It has now been found that the novel active compound combinations comprising methoximinoacetamide derivatives of the general formula (I),

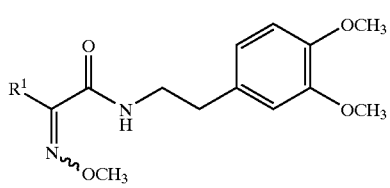

(I)

in which
R¹ represents unsubstituted or fluorine-, chlorine-, bromine-, methyl-, ethyl-, n- or i-propyl-, n-, i- or t-butyl-, methoxy-, ethoxy- or phenoxy-substituted phenyl, 2-naphthyl, 1,2,3,4-tetrahydronaphthyl, indanyl, 2-benzofuranyl, 2-benzothienyl, 2-thienyl or 2-furanyl, and
(1) a triazole derivative of the formula

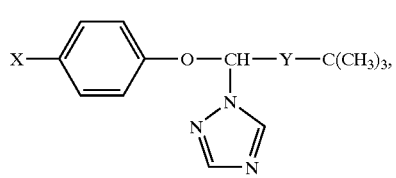

(II)

in which
X represents chlorine or phenyl and

Y represents

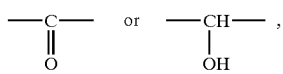

and/or (2) the triazole derivative of the formula

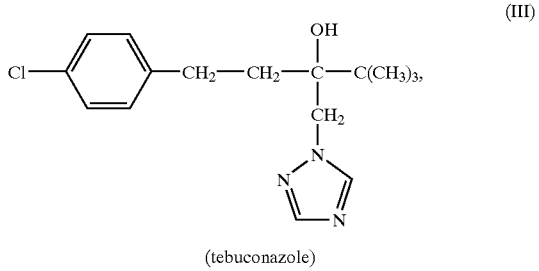

(tebuconazole)

and/or (3) an aniline derivative of the formula

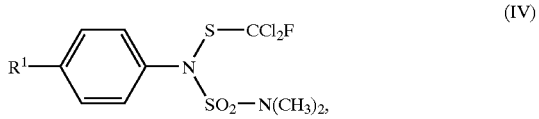

(IV)

in which
R¹ represents hydrogen or methyl, and/or (4) N-[1-(4-chloro-phenyl)-ethyl]-2,2-dichloro-1-ethyl-3-methyl-cyclopropane-carboxamide of the formula

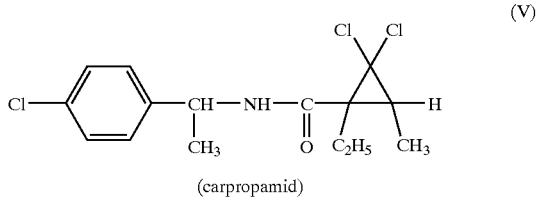

(carpropamid)

and/or (5) the zinc propylene-1,2-bis-(dithiocarbamidate) of the formula

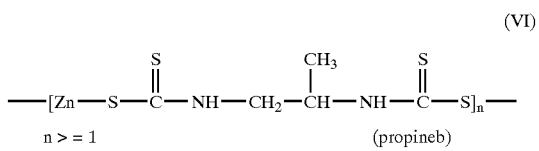

and/or (6) at least one thiocarbamate of the formula (VII)

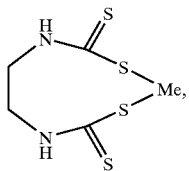

Me=Zn or Mn or a mixture of Zn and Mn and/or (7) the aniline derivative of the formula (VIII)

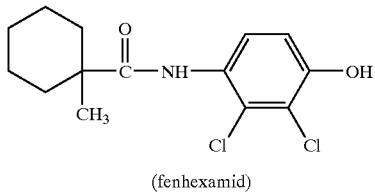

(fenhexamid)

and/or (8) the compound of the formula (IX)

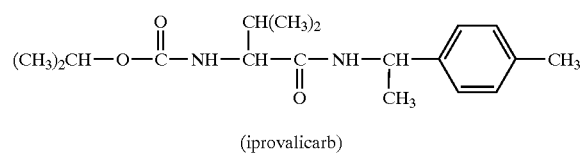

(iprovalicarb)

and/or (9) the benzothiadiazole derivative of the formula (X)

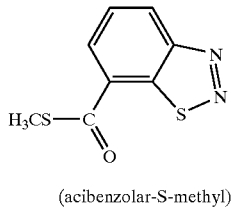

(acibenzolar-S-methyl)

and/or

(10) the 8-t-butyl-2-(N-ethyl-N-n-propyl-amino)-methyl-1,4-dioxaspiro[5,4]-decane of the formula (XI)

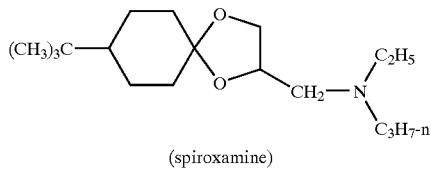

(spiroxamine)

and/or

(11) the compound of the formula (XII)

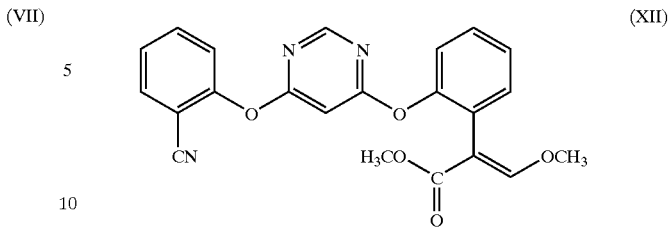

(azoxystrobin)

and/or

(12) the compound of the formula (XIII)

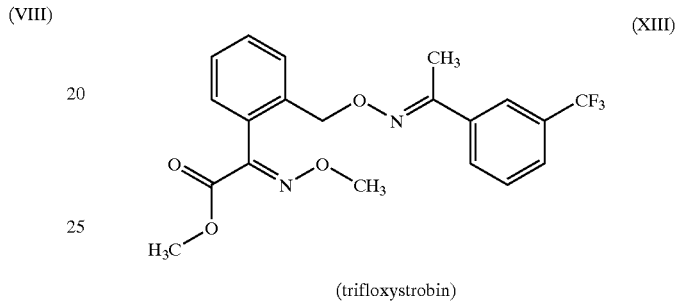

(trifloxystrobin)

and/or

(13) the compound of the formula (XIV)

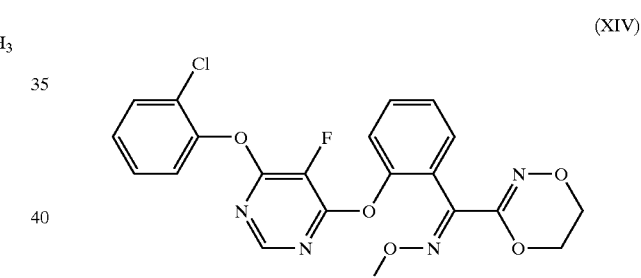

and/or

(14) the cyanoxime derivative of the formula (XV)

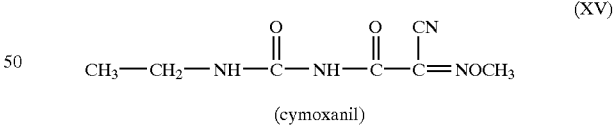

(cymoxanil)

and/or

(15) a pyrimidine derivative of the formula (XVI)

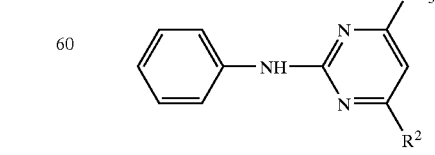

in which
$R^2$ represents methyl or cyclopropyl, and/or

(16) an aniline derivative of the formula (XVII)

(metalaxyl or metalaxyl M)

and/or

(17) the morpholine derivative of the formula (XVIII)

(dimetomorph)

and/or

(18) the phthalimide derivative of the formula (XIX)

(folpet)

and/or

(19) the phosphorus compound of the formula (XX)

(fosetyl-Al)

and/or

(20) the hydroxyethyl-triazole derivative of the formula (XXI)

and/or
(21) the 1-[(6-chloro-3-pyridinyl)-methyl]-N-nitro-2-imidazolidinimine of the formula (XXII)

(imidacloprid)

and/or
(22) the oxazolidinedione of the formula (XXIII)

(famoxadone)

and/or
(23) the benzamide derivative of the formula (XXIV)

(zoxamide)

and/or
(24) a guanidine derivative of the formula (XXV)

$$R^3-\underset{H}{N}-(CH_2)_8-[\underset{}{\overset{R^3}{N}}-(CH_2)_8]_m-\underset{}{\overset{R^3}{N}}-H$$

$$x(2+m)CH_3COOH$$

in which
m represents integers from 0 to 5 and
$R^3$ represents hydrogen (17 to 23%) or the radical of the formula

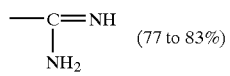 (77 to 83%)

and/or

(25) the triazole derivative of the formula

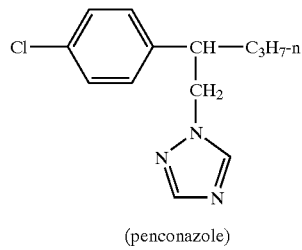 (XXVI)

(penconazole)

and/or

(26) the halogeno-benzimidazole of the formula

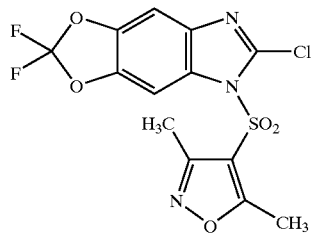 (XXVII)

and/or

(27) the halogenopyrimidine of the formula

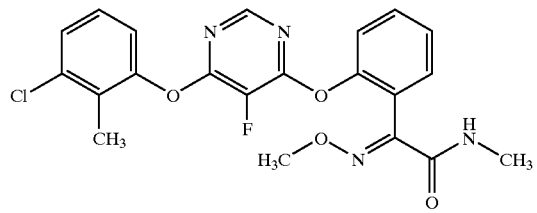 (XXVIII)

and/or

(28) the tetrachloro-isophthalo-dinitrile of the formula

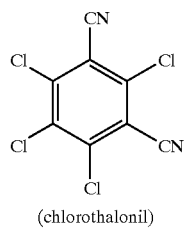 (XXIX)

(chlorothalonil)

and/or

(29) the compound of the formula

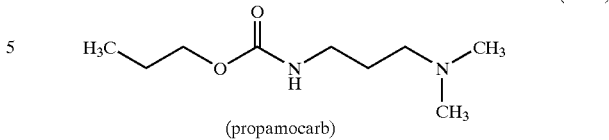 (XXX)

(propamocarb)

and/or

(30) the pyridinamine of the formula

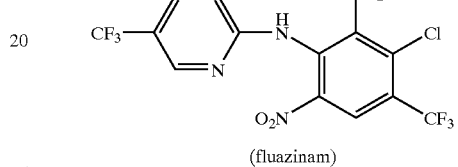 (XXXI)

(fluazinam)

and/or

(31) the thiazolecarboxamide of the formula

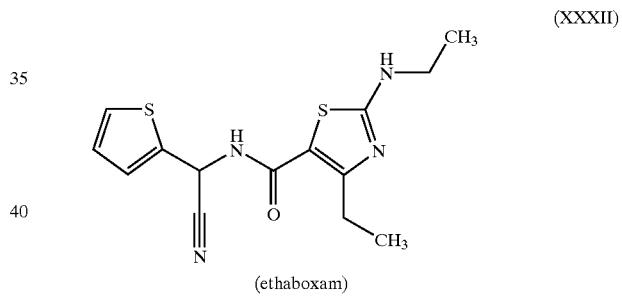 (XXXII)

(ethaboxam)

and/or

(32) the sulphonamide of the formula

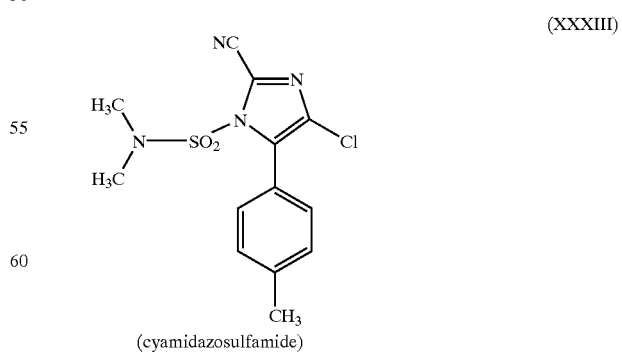 (XXXIII)

(cyamidazosulfamide)

and/or

(33) the compound of the formula

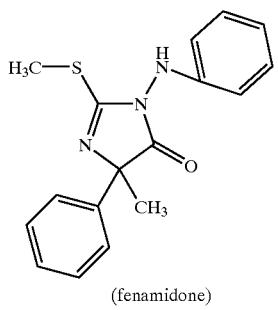

(fenamidone)

and/or

(34) the compound of the formula

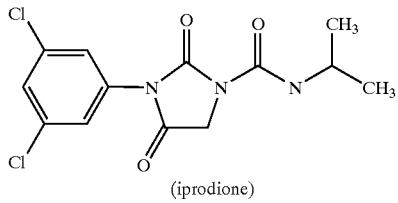

(iprodione)

and/or

(35) the compound of the formula

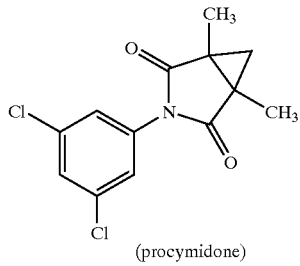

(procymidone)

and/or

(36) the diamide of the formula

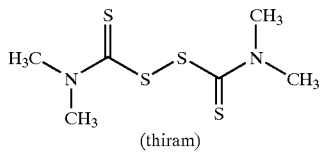

(thiram)

and/or

(37) the methoxyacrylate derivative of the formula

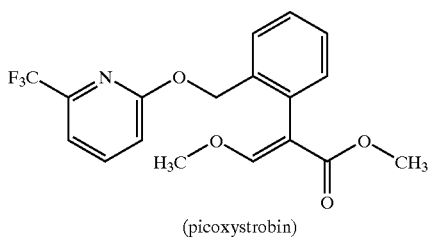

(picoxystrobin)

and/or

(38) the quinoline derivative of the formula

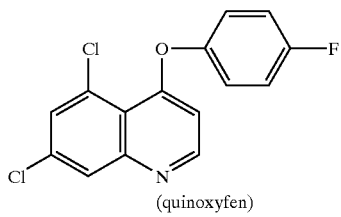

(quinoxyfen)

and/or

(39) the phenylamide derivative of the formula

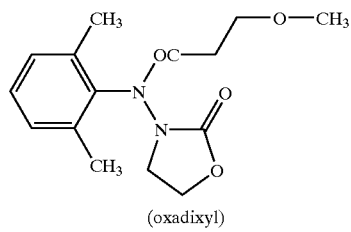

(oxadixyl)

and/or

(40) the phenylamide derivative of the formula

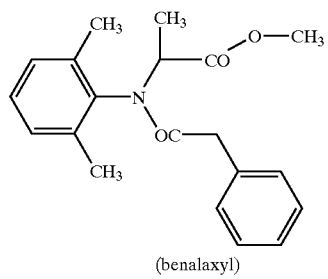

(benalaxyl)

and/or

(41) the dicarboxime derivative of the formula (XXXXII)

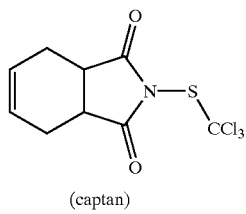

(captan)

and/or

(42) the phosphonic acid of the formula (XXXXIII)

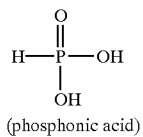

(phosphonic acid)

and/or

(43) the pyrrole derivative of the formula (XXXXIV)

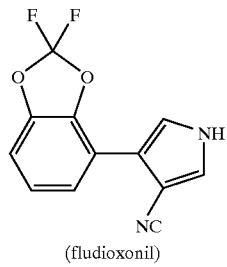

(fludioxonil)

and/or

(44) the phenyl carbonate of the formula (XXXXV)

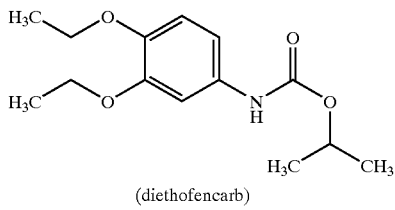

(diethofencarb)

and/or (45)

a) copper oxychloride (XXXXVIa)

b) copper hydroxide (XXXXVIb)

and/or

(46) the imidazole derivative of the formula (XXXXVII)

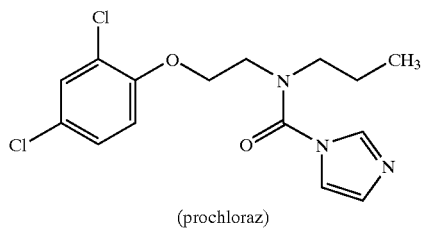

(prochloraz)

and/or

(47) a triazole derivative of the formula (XXXXVIIIa)

a)

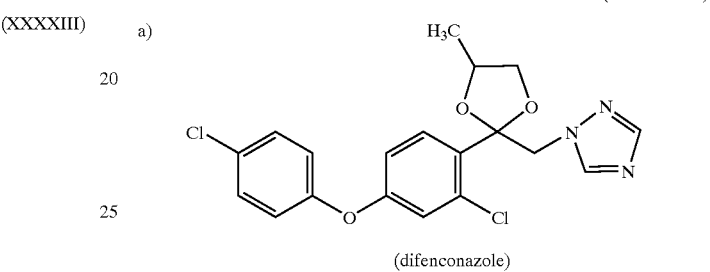

(difenconazole)

and/or b)

(XXXXVIIIb)

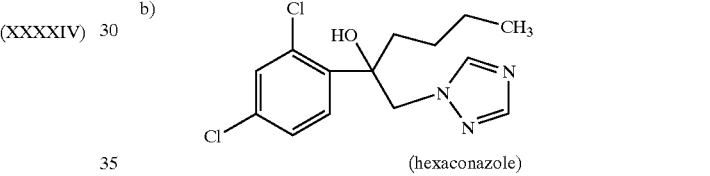

(hexaconazole)

and/or c)

(XXXXVIIIc)

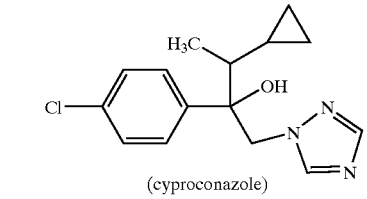

(cyproconazole)

and/or d)

(XXXXVIIId)

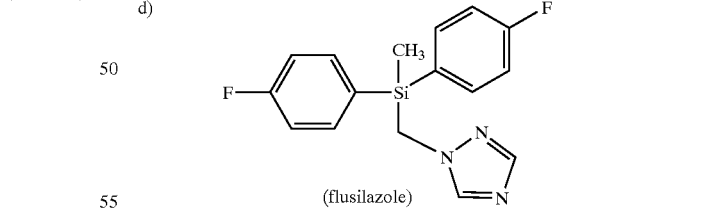

(flusilazole)

and/or e)

(XXXXVIIIe)

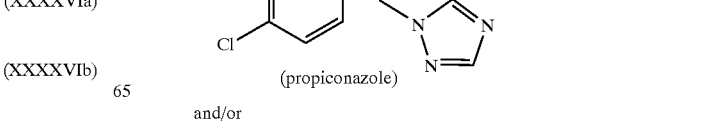

(propiconazole)

and/or f) 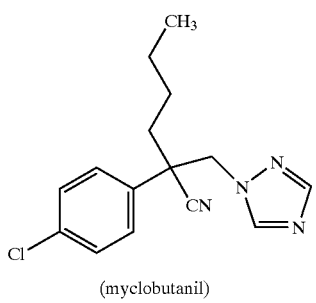
(myclobutanil)

and/or g) 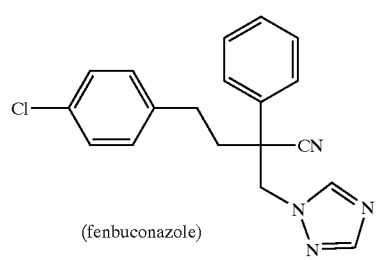
(fenbuconazole)

and/or h) 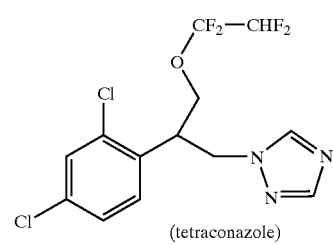
(tetraconazole)

and/or i) 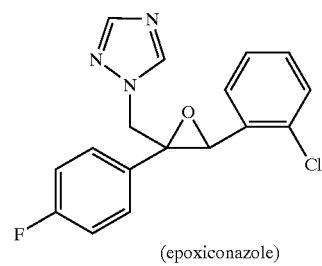
(epoxiconazole)

and/or

(48) the compound of the formula (XXXXIX)

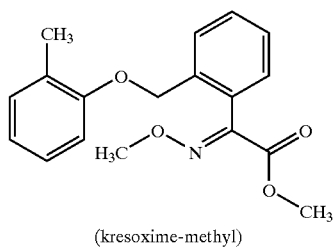
(kresoxime-methyl)

and/or

(49) N-methyl-2-(methoxyimino)-2-[2-([1-(3-tri-fluoro-methyl-phenyl)ethoxy]iminomethyl)phenyl]acetamide of the formula (XXXXX)

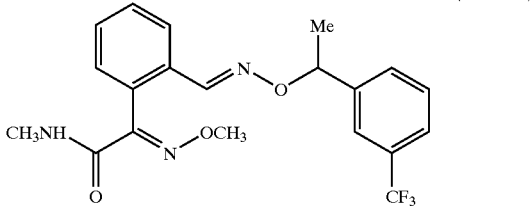

and/or

(50) 2-[2-([2-phenyl-2-methoxyimino-1-methylethyl]-imino-oxymethyl)phenyl]-2-methoxyimino-N-methylacetamide of the formula (XXXXXI)

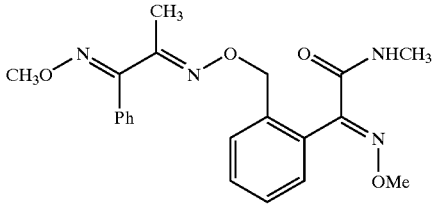

and/or

(51) 2-[2-([2-(4-fluorophenyl)-2-methoxyimino-1-methylethyl]-iminooxymethyl)phenyl]-2-methoxyimino-N-methyl-acetamide of the formula (XXXXXII)

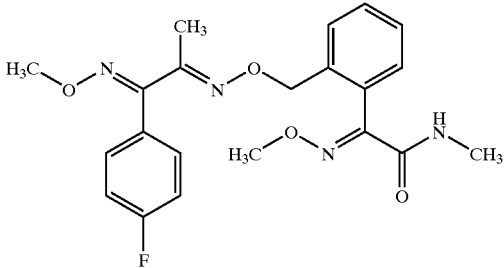

and/or

(52) 2-[4-methoxy-3-(1-methylethoxy)-1,4-diazabuta-1,3-dienyl-oxymethyl]phenyl-2-methoximino-N-methyl-acetamide of the formula (XXXXXIII)

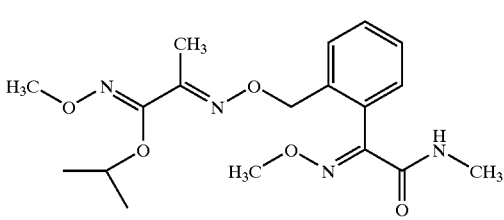

and/or

(53) methyl N-(2-[1-(4-chlorophenyl)pyrazol-3-yloxymethyl]phenyl)-N-methoxycarbamate of the formula

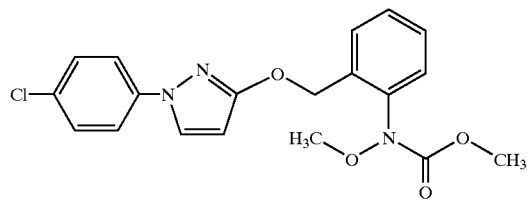
(XXXXXIV)

and/or

(54) 2,4-dihydro-5-methoxy-2-methyl-4-[2-([([1-(3-trifluoromethyl-phenyl)ethylidene]amino)oxy]methyl)phenyl]-3H-1,2,4-triazol-3-one of the formula

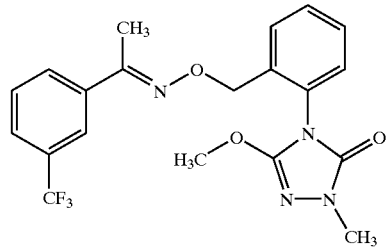
(XXXXXV)

and/or

(55) the compound of the formula

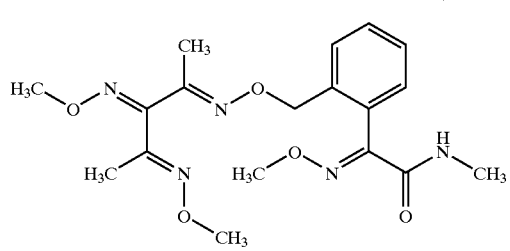
(XXXXXVI)

and/or

(56) the compound of the formula

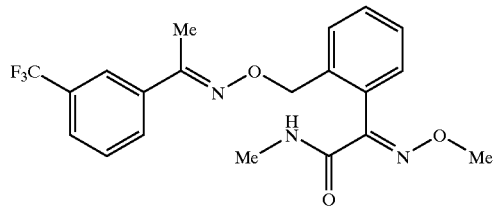
(XXXXXVII)

and/or

(57) a compound of the formula

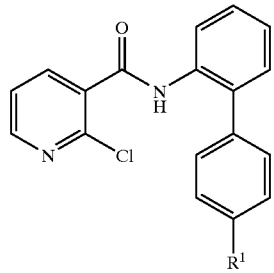
(XXXXXVIII)

in which
R$^1$ represents fluorine (XXXXXVIIIa) or chlorine (XXXXXVIIIb), and/or

(58) a compound of the formula

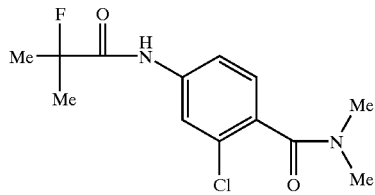
(XXXXXIX)

have very good fungicidal properties.

Surprisingly, the fungicidal activity of the active compound combinations according to the invention is considerably higher than the sum of the activities of the individual active compounds. Thus, an unforeseeable, true synergistic effect is present, and not just an addition of activities.

From the structural formula of the active compound of the formula (I), it can be seen that the compound can be present as E or Z isomers. Accordingly, the product can be present as a mixture of different isomers or else in the form of a single isomer. Preference is given to compounds of the formula (I) in which the compounds of the formula (I) are present as E isomer.

Preference is given to compounds of the formula (I), in which R$^1$ represents unsubstituted or fluorine-, chlorine-, bromine-, methyl- or ethyl-substituted phenyl, 2-naphthyl, 1,2,3,4-tetrahydronaphthyl, indanyl, 2-thienyl or 2-furanyl.

Particular preference is given to compounds of the formula (I) in which R$^1$ represents unsubstituted or fluorine-, chlorine-, bromine-, methyl- or ethyl-substituted phenyl, 2-naphthyl, 1,2,3,4-tetrahydronaphthyl or indanyl.

Specifically, mention may be made of the compounds of the formula (Ia)

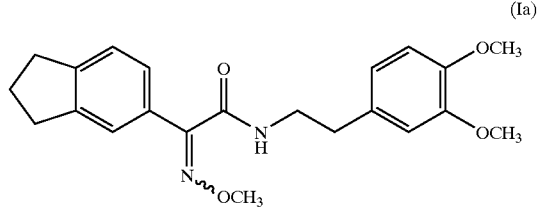
(Ia)

of the formula (Ib)

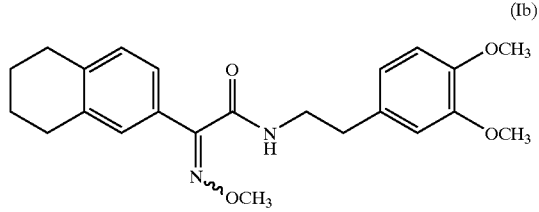
(Ib)

of the formula (Ic)

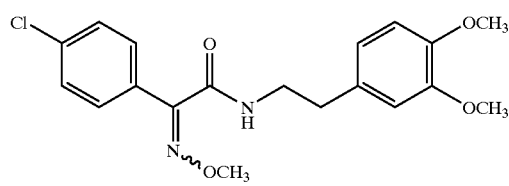
(Ic)

of the formula (Id)

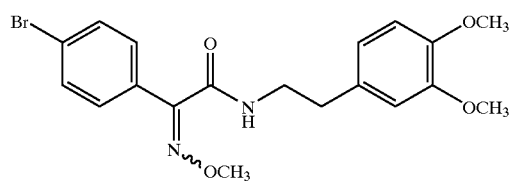
(Id)

of the formula (Ie)

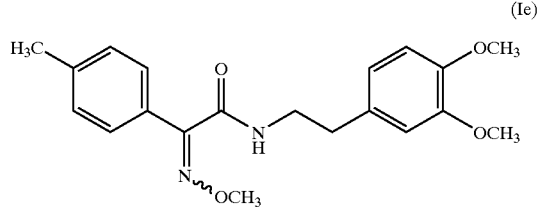
(Ie)

and of the formula (If)

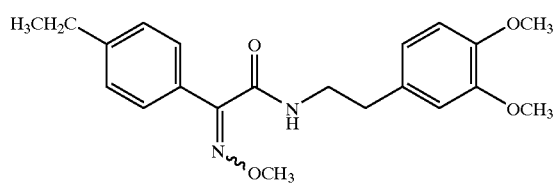
(If)

and their isomers, as described above.

The formula (II) includes the compounds
1-(4-chloro-phenoxy)-3,3-dimethyl-1-(1,2,4-triazol-1-yl)-butan-2-one of the formula

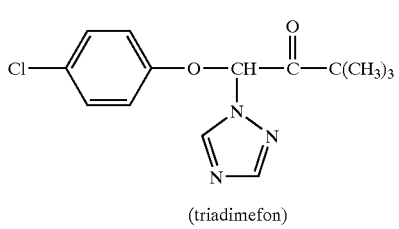
(IIa)

(triadimefon)

1-(4-chloro-phenoxy)-3,3-dimethyl-1-(1,2,4-triazol-1-yl)-butan-2-ol of the formula

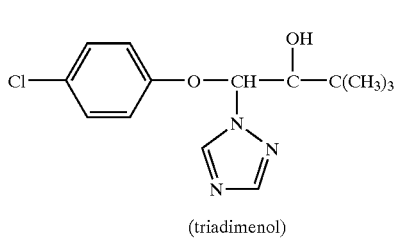
(IIb)

(triadimenol)

and
1-(4-phenyl-phenoxy)-3,3-dimethyl-1-(1,2,4-triazol-1-yl)-butan-2-ol of the formula

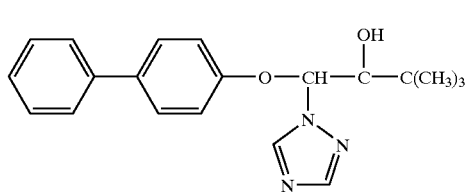
(IIc)

(bitertanol)

The formula (IV) includes the aniline derivatives of the formulae

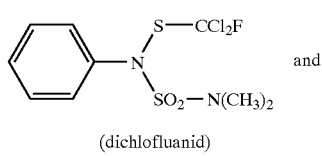
(IVa)

(dichlofluanid)

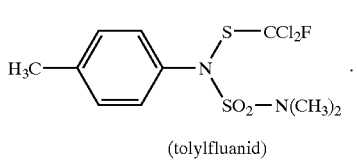
(IVb)

(tolylfluanid)

It is evident from the structural formula for the active compound of the formula (V) that the compound has three asymmetrically substituted carbon atoms. The product may therefore be present as a mixture of different isomers, or else in the form of a single component. Particular preference is given to the compounds
N-(R)-[1-(4-chloro-phenyl)-ethyl]-(1S)-2,2-dichloro-1-ethyl-3t-methyl-1R-cyclopro-panecarboxamide of the formula

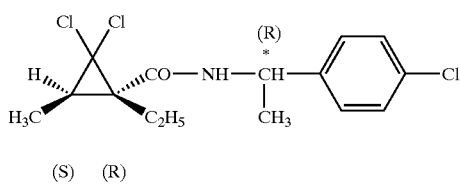

(Va)

and
N-(R)-[1-(4-chloro-phenyl)-ethyl]-(1R)-2,2-dichloro-1-ethyl-3t-methyl-1R-cyclopro-panecarboxamide of the formula

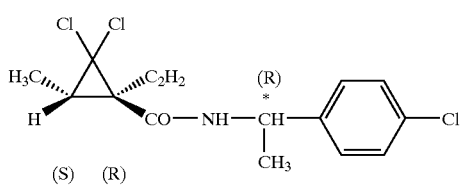

(Vb)

The formula (VII) includes the compounds
(VIIa) Me=Zn (zineb),
(VIIb) Me=Mn (maneb) and
(VIIc) mixture of (VIIa) and (VIIb) (mancozeb).
The formula (XVI) includes the compounds
(XVIa) $R^2$=CH$_3$ (pyrimethanil) and

(XVIb)

The hydroxyethyl-triazole derivative of the formula (XXI) can be present in the "thiono" form of the formula

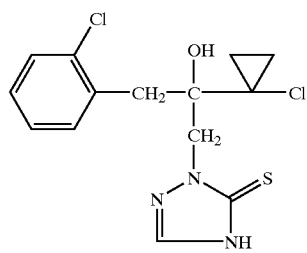

(XXI)

or in the tautomeric "mercapto" form of the formula

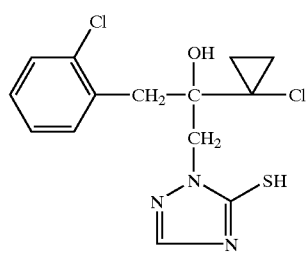

(XXIb)

For simplicity's sake, only the "thiono" form is given in each case.

The guanidine derivative of the formula (XXV) is a substance mixture with the common name guazatine.

The components which are present in the active combinations according to the invention are also known.

Specifically, the active compounds are described in the following publications:
(1) compounds of the formula (II)
  DE-A 22 01 063
  DE-A 23 24 010
(2) compound of the formula (III)
  EP-A 0 040 345
(3) compounds of the formula (IV)
  Pesticide Manual, 9th Ed. (1991), pages 249 and 827
(4) compound of the formula (V) and individual derivatives thereof
  EP-A 0 341 475
(5) compound of the formula (VI)
  Pesticide Manual, 9th Ed. (1991), page 726
(6) compounds of the formula (VII)
  Pesticide Manual, 9th Ed. (1991), pages 529, 531 and 866
(7) compound of the formula (VW)
  EP-A 0 339 418
(8) compound of the formula (IX)
  EP-A 0 472 996
(9) compound of the formula (X)
  EP-A 0 313 512
(10) compound of the formula (XI)
  EP-A 0 281 842
(11) compound of the formula (XII)
  EP-A 0 382 375
(12) compound of the formula (XIII)
  EP-A-460 575
(13) compound of the formula (XIV)
  DE-A 196 02 095
(14) compound of the formula (XV)
  Pesticide Manual, 9th Ed. (1991), page 206
(15) compounds of the formula (XVI)
  EP-A 0 270 111
  EP-A 0 310 550
(16) compound of the formula (XVII)
  Pesticide Manual, 9th Ed. (1991), page 554
(17) compound of the formula (XVIII)
  EP-A0219756
(18) compound of the formula (XIX)
  Pesticide Manual, 9th Ed. (1991), page 431
(19) compound of the formula (XX)
  Pesticide Manual, 9th Ed. (1991), page 443
(20) compound of the formula (XXI)
  WO 96-16048
(21) compound of the formula (XXII)
  Pesticide Manual, 9th Ed. (1991), page 491
(22) compound of the formula (XXIII)
  EP-A 0 393 911
(23) compound of the formula (XXIV)
  EP-A 0 600 629
(24) substance of the formula (XXV)
  Pesticide Manual, 9th Ed. (1991), page 461
(25) compound of the formula (XXVI)
  Pesticide Manual, 9th Ed. (1991), page 654
(26) compound of the formula (XXVII)
  WO 97-06171
(27) compound of the formula (XXVIII)
  DE-A1-196 46 407, EP-B-0 712 396
(28) compound of the formula (XXIX)
  U.S. Pat. No. 3,290,353

(29) compound of the formula (XXX)
   DE-A-156 7169
(30) compound of the formula (XXXI)
   EP-A-0 031 257
(31) compound of the formula (XXXII)
   EP-A-0 639 547
(32) compound of the formula (XXXIII)
   EP-A-0 298 196
(33) compound of the formula (XXXIV)
   EP-A-0 629 616
(34) compound of the formula (XXXV)
   DE-A-2 149 923
(35) compound of the formula (XXXVI)
   DE-A-2 012 656
(36) compound of the formula (XXXVII)
   U.S. Pat. No. 1,972,961
(37) compound of the formula (XXXVIII)
   EP-A-326 330
(38) compound of the formula (XXXIX)
   EP-A 278 595
(39) compound of the formula (XXXX)
   DE-A-3 030 026
(40) compound of the formula (XXXXI)
   DE-A-2 903 612
(41) compound of the formula (XXXXII)
   U.S. Pat. No. 2,553,770
(42) compound of the formula (XXXXIII)
   known and commercially available
(43) compound of the formula (XXXXIV)
   EP-A-206 999
(44) compound of the formula (XXXXV)
   EP-A-78 663
(45) compounds of the formulae (XXXXVIa) and (XXXXVIb)
   known and commercially available
(46) compound of the formula (XXXXVII)
   DE-A-2 429 523
(47)
   a) compound of the formula (XXXXVIIIa)
      EP-A-112 284
   b) compound of the formula (XXXXVIIIb)
      DE-A-3 042 303
   c) compound of the formula (XXXXVIIIc)
      DE-A-3 406 993
   d) compound of the formula (XXXXVIIId)
      EP-A-68 813
   e) compound of the formula (XXXXVIIIe)
      DE-A-2551560
   f) compound of the formula (XXXXVIIIf)
      EP-A-145 294
   g) compound of the formula (XXXXVIIIg)
      DE-A-3 721 786
   h) compound of the formula (XXXXVIIIh)
      EP-A-234 242
   i) compound of the formula (XXXXVIIIi)
      EP-A-196 038
(48) compound of the formula (XXXXIX)
   EP-A-253 213
(49) compound of the formula (XXXXX)
   EP-A-596 254
(50) compound of the formula (XXXXXI)
   WO 95/21154
(51) compound of the formula (XXXXXII)
   WO 95/21154
(52) compound of the formula (XXXXXIII)
   DE-A-195 28 651
(53) compound of the formula (XXXXXIV)
   DE-A-44 23 612
(54) compound of the formula (XXXXXV)
   WO 98/23155
(55) compound of the formula (XXXXXVI)
   WO 97/15552
(56) compound of the formula (XXXXXVII)
   EP-A-569 384
(57) compounds of the formula (XXXXXVIII)
   EP-A-545 099
(58) compound of the formula (XXXXXVIX)
   EP-A-600 629.

In addition to an active compound of the formula (1), the active compound combinations according to the invention comprise at least one active compound of the compounds of groups (1) to (58). Additionally, they may comprise further fungicidally active additives.

The synergistic effect is particularly pronounced when the active compounds in the active compound combinations according to the invention are present in certain weight ratios. However, the weight ratios of the active compounds in the active compound combinations can be varied within a relatively wide range. In general,
from 0.1 to 50 parts by weight, preferably from 0.2 to 20 parts by weight, of active compound of group (1),
from 0.1 to 50 parts by weight, preferably from 0.2 to 20 parts by weight, of active compound of group (2),
from 0.1 to 150 parts by weight, preferably from 1 to 100 parts by weight, of active compound of group (3),
from 0.1 to 10 parts by weight, preferably from 0.2 to 5 parts by weight, of active compound of group (4),
from 0.1 to 150 parts by weight, preferably from 1 to 100 parts by weight, of active compound of group (5),
from 0.1 to 150 parts by weight, preferably from 1 to 100 parts by weight, of active compound of group (6),
from 0.1 to 50 parts by weight, preferably from 0.2 to 20 parts by weight, of active compound of group (7),
from 0.1 to 50 parts by weight, preferably from 0.2 to 20 parts by weight, of active compound of group (8),
from 0.02 to 50 parts by weight, preferably from 0.1 to 10 parts by weight, of active compound of group (9),
from 0.1 to 50 parts by weight, preferably from 0.2 to 20 parts by weight, of active compound of group (10),
from 0.1 to 50 parts by weight, preferably from 0.2 to 20 parts by weight, of active compound of group (11),
from 0.1 to 50 parts by weight, preferably from 0.2 to 20 parts by weight, of active compound of group (12),
from 0.1 to 50 parts by weight, preferably from 0.2 to 20 parts by weight, of active compound of group (13),
from 0.1 to 50 parts by weight, preferably from 0.2 to 20 parts by weight, of active compound of group (14),
from 0.1 to 50 parts by weight, preferably from 0.2 to 20 parts by weight, of active compound of group (15),
from 0.1 to 50 parts by weight, preferably from 0.2 to 20 parts by weight, of active compound of group (16),
from 0.1 to 50 parts by weight, preferably from 0.2 to 20 parts by weight, of active compound of group (17),
from 0.1 to 150 parts by weight, preferably from 1 to 100 parts by weight, of active compound of group (18),
from 0.1 to 150 parts by weight, preferably from 1 to 100 parts by weight, of active compound of group (19),
from 0.1 to 50 parts by weight, preferably from 0.2 to 20 parts by weight, of active compound of group (20), from 0.05 to 20 parts by weight, preferably from 0.1 to 10 parts by weight, of active compound of group (21),
from 0.1 to 50 parts by weight, preferably from 0.2 to 20 parts by weight, of active compound of group (22),
from 0.1 to 50 parts by weight, preferably from 0.2 to 20 parts by weight, of active compound of group (23),
from 0.2 to 50 parts by weight, preferably from 0.04 to 10 parts by weight, of active compound of group (24),
from 0.1 to 50 parts by weight, preferably from 0.2 to 20 parts by weight, of active compound of group (25),
from 0.05 to 50 parts by weight, preferably from 0.1 to 20 parts by weight, of active compound of group (26),
from 0.1 to 50 parts by weight, preferably from 0.2 to 20 parts by weight, of active compound of group (27),
from 0.1 to 150 parts by weight, preferably from 1 to 100 parts by weight, of active compound of group (28),
from 0.1 to 150 parts by weight, preferably from 1 to 100 parts by weight, of active compound of group (29),
from 0.1 to 50 parts by weight, preferably from 0.2 to 20 parts by weight, of active compound of group (30),
from 0.1 to 50 parts by weight, preferably from 0.2 to 20 parts by weight, of active compound of group (31),
from 0.1 to 50 parts by weight, preferably from 0.2 to 20 parts by weight, of active compound of group (32),
from 0.1 to 50 parts by weight, preferably from 0.2 to 20 parts by weight, of active compound of group (33),
from 0.1 to 50 parts by weight, preferably from 0.2 to 20 parts by weight, of active compound of group (34),
from 0.1 to 50 parts by weight, preferably from 0.2 to 20 parts by weight, of active compound of group (35),
from 0.1 to 150 parts by weight, preferably from 1 to 100 parts by weight, of active compound of group (36),
from 0.1 to 50 parts by weight, preferably from 0.2 to 20 parts by weight, of active compound of group (37),
from 0.1 to 50 parts by weight, preferably from 0.2 to 20 parts by weight, of active compound of group (38),
from 0.1 to 50 parts by weight, preferably from 0.2 to 20 parts by weight, of active compound of group (39),
from 0.1 to 50 parts by weight, preferably from 0.2 to 20 parts by weight, of active compound of group (40),
from 0.1 to 150 parts by weight, preferably from 1 to 100 parts by weight, of active compound of group (41),
from 0.1 to 150 parts by weight, preferably from 1 to 100 parts by weight, of active compound of group (42),
from 0.1 to 50 parts by weight, preferably from 0.2 to 20 parts by weight, of active compound of group (43),
from 0.1 to 50 parts by weight, preferably from 0.2 to 20 parts by weight, of active compound of group (44),
from 0.1 to 150 parts by weight, preferably from 1 to 100 parts by weight, of active compound of group (45),
from 0.1 to 50 parts by weight, preferably from 0.2 to 20 parts by weight, of active compound of group (46),
from 0.1 to 50 parts by weight, preferably from 0.2 to 20 parts by weight, of active compound of group (47a),
from 0.1 to 50 parts by weight, preferably from 0.2 to 20 parts by weight, of active compound of group (47b),
from 0.1 to 50 parts by weight, preferably from 0.2 to 20 parts by weight, of active compound of group (47c),
from 0.1 to 50 parts by weight, preferably from 0.2 to 20 parts by weight, of active compound of group (47d),
from 0.1 to 50 parts by weight, preferably from 0.2 to 20 parts by weight, of active compound of group (47e),
from 0.1 to 50 parts by weight, preferably from 0.2 to 20 parts by weight, of active compound of group (47f),
from 0.1 to 50 parts by weight, preferably from 0.2 to 20 parts by weight, of active compound of group (47 g),
from 0.1 to 50 parts by weight, preferably from 0.2 to 20 parts by weight, of active compound of group (47 h),
from 0.1 to 50 parts by weight, preferably from 0.2 to 20 parts by weight, of active compound of group (47i),
from 0.1 to 50 parts by weight, preferably from 0.2 to 20 parts by weight, of active compound of group (48),
from 0.1 to 50 parts by weight, preferably from 0.2 to 20 parts by weight, of active compound of group (49),
from 0.1 to 50 parts by weight, preferably from 0.2 to 20 parts by weight, of active compound of group (50),
from 0.1 to 50 parts by weight, preferably from 0.2 to 20 parts by weight, of active compound of group (51),
from 0.1 to 50 parts by weight, preferably from 0.2 to 20 parts by weight, of active compound of group (52),
from 0.1 to 50 parts by weight, preferably from 0.2 to 20 parts by weight, of active compound of group (53),
from 0.1 to 50 parts by weight, preferably from 0.2 to 20 parts by weight, of active compound of group (54),
from 0.1 to 50 parts by weight, preferably from 0.2 to 20 parts by weight, of active compound of group (55),
from 0.1 to 50 parts by weight, preferably from 0.2 to 20 parts by weight, of active compound of group (56),
from 0.1 to 50 parts by weight, preferably from 0.2 to 20 parts by weight, of active compound of group (57),
from 0.1 to 50 parts by weight, preferably from 0.2 to 20 parts by weight, of active compound of group (58)
are present per part by weight of active compound of the formula (I).

The active compound combinations according to the invention have very good fungicidal properties and can be employed for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling *Phytophthora infestans* and *Plasmopara viticola*.

The fact that the active compound combinations are well tolerated by plants at the concentrations required for controlling plant diseases permits the treatment of above-ground parts of plants, of propagation stock and seeds, and of the soil. The active compound combinations according to the invention can be used for foliar application or else as seed dressing.

The active compound combinations according to the invention may also be employed to increase the yield of crops. Moreover, they have reduced toxicity and are tolerated well by plants.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

As already mentioned above, it is possible to treat all plants and their parts according to the invention. In a preferred embodiment, wild plant species and plant varieties, or those obtained by conventional biological breeding, such as crossing or protoplast fusion, and parts thereof, are treated. In a further preferred embodiment, transgenic plants and plant varieties obtained by genetical engineering, if appropriate in combination with conventional methods (Genetic Modified Organisms), and parts thereof are treated. The term "parts" or "parts of plants" or "plant parts" has been explained above.

Particularly preferably, plants of the plant varieties which are in each case commercially available or in use are treated according to the invention. Plant varieties are understood as meaning plants having certain properties (traits) that may be obtained by conventional breeding, by mutagenesis or by recombinant DNA techniques. These may be varieties, bio- or genotypes.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to draught or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant varieties (i.e. those obtained by genetical engineering) which are preferred and are to be treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants against fungi, bacteria and viruses by Systematic Acquired Resistance (SAR), systemine, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene).

The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant varieties having these or still to be developed genetic traits, which plants will be developed and/or marketed in the future.

The plants listed can be treated according to the invention in a particularly advantageous manner with the compounds of the general formula I or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The treatment of the plants and parts of plants according to the invention with the active compounds is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compound combinations according to the invention can be converted to the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

The active compound combinations according to the invention, as such or in their formulations, can also be applied in a mixture with known fungicides, bactericides, acaricides, nematicides or insecticides, to broaden the activity spectrum or to prevent the development of resistance, for example. In many cases, synergistic effects are obtained, i.e. the activity of the mixture is greater than the activity of the individual components.

A mixture with other known active compounds such as herbicides or with fertilizers and growth regulators is also possible.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combinations according to the invention, the application rates can be varied within a relatively wide range, depending on the kind of application. In the treatment of parts of plants, the application rates of the active compound combination are generally between 0.1 and 10,000 g/ha, preferably between 10 and 1000 g/ha. In the treatment of seeds, the application rates of the active compound combination are generally between 0.001 and 50 g per kilogram of seed, preferably between 0.01 and 10 g per kilogram of seed. In the treatment of the soil, the application rates of the active compound combination are generally between 0.1 and 10,000 g/ha, preferably between 1 and 5000 g/ha.

The good fungicidal activity of the active compound combinations according to the invention is evident from the examples below. While the individual active compounds exhibit weaknesses with regard to the fungicidal activity, the combinations have an activity which exceeds the sum of individual activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", Weeds 15, (1967), 20–22):

If

X is the efficacy when applying active compound A at an application rate of m g/ha, Y is the efficacy when applying active compound B at an application rate of n g/ha and E is the efficacy when applying the active compounds A and B at an application rate of m and n g/ha, then $$E = X + Y - \frac{X \cdot Y}{100}$$

The efficacy is calculated in %. 0% is an efficacy which corresponds to that of the control, whereas an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The example that follows illustrates the invention. However, the invention is not limited to the example.

EXAMPLE

Plasmopara Test (Grapevine)/Protective

Solvent: 49 parts by weight of acetone

Emulsifier: 1 part by weight of alkyl-aryl polyglycol ether

To produce a suitable preparation of active compound, 1 part by weight of active compound or active compound combination is mixed with the stated amounts of solvent and emulsifier, and the concentrate is diluted with water to the desired concentration, or a commercially available formulation of active compound or active compound combination is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at approximately 20° C. and 100% relative atmospheric humidity for 1 day. The plants are then placed in a greenhouse at approximately 21° C. and approximately 90% atmospheric humidity for 4 days. The plants are then moistened and then placed in an incubation cabin for 1 day.

Evaluation is carried out 6 days after the inoculation. 0% means an efficacy which corresponds to that of the control, whereas an efficacy of 100% means that no infection is observed.

The expected activity for a given combination of two active compounds can be calculated as follows (cf. Colby, S. R., "Calculating Synergistic and Antagonistic Responses of Herbicide Combinations", Weeds 15, (1967), 20–22);

If

X is the efficacy when applying active compound A at an application rate of m g/ha, Y is the efficacy when applying active compound B at an application rate of n g/ha and E is the efficacy when applying the active compounds A and B at an application rate of m and n g/ha, then $$E = X + Y - \frac{X \cdot Y}{100}$$

The efficacy is calculated in %. 0% is an efficacy which corresponds to that of the control, whereas an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The table below shows clearly that the efficacy observed for the active compound combination according to the invention is greater than the efficacy that was calculated, i.e. a synergistic effect exists.

TABLE

Plasmopara test (grapevine)/protective

| Active compound | Active compound application rate in g/ha | % efficacy |
|---|---|---|
| Known: | | |
| Ib | 10 | 66 |
| Copper oxychloride (XXXXVIa) | 100 | 26 |

| | Mixing ratio | Active compound application rate in g/ha | Actual efficacy | Expected efficacy, calculated using Colby's formula |
|---|---|---|---|---|
| Mixture according to the invention: | | | | |
| (Ib) + Copper oxychlonde (XXXXVIa) | 1:10 | 10 + 100 | 89 | 75 |

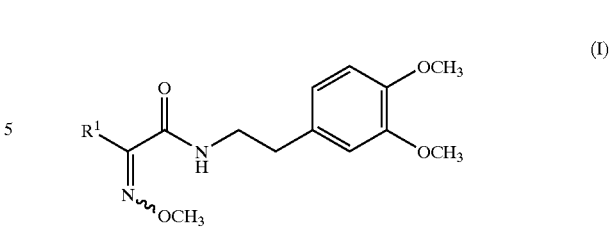

in which R¹ represents unsubstituted phenyl, 2-naphthyl, 1,2,3,4-tetrahydro-naphthyl, or indanyl, or fluorine-, chlorine-, bromine-, methyl-, ethyl-, n- or i-propyl-, n-, i-, or t-butyl-, methoxy-, ethoxy-, or phenoxy-substituted phenyl, 2-naphthyl, 1,2,3,4-tetrahydronaphthyl, or indanyl, and (b) at least one ingredient selected from the group consisting of copper oxychloride, copper hydroxide and mixtures thereof, wherein the ratio of the active compound of formula (I) of component (a) to ingredient (b) is from 1:0.1 to 1:150.

What is claimed is:

1. An active compound combination comprising
(a) at least one compound of the formula (I), 2. An active compound combination according to claim 1 wherein the compound of the formula (I) is a compound of the formula (Ia)

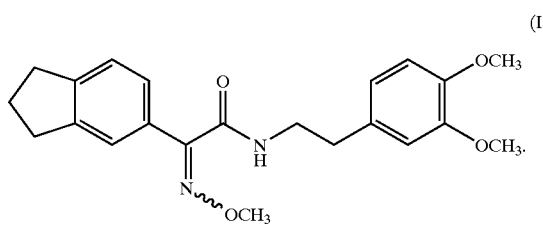
(Ia)

3. An active compound combination according to claim 1 wherein the compound of the formula (I) is a compound of the formula (Ib)

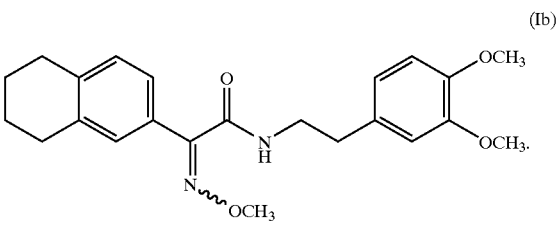
(Ib)

4. An active compound combination according to claim 1 wherein the compound of the formula (I) is a compound of the formula (Ic)

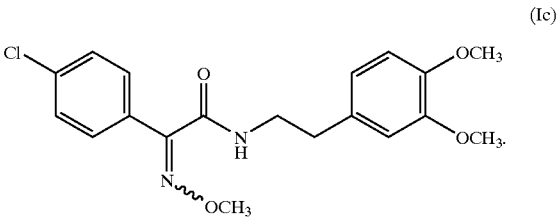
(Ic)

5. An active compound combination according to claim 1 wherein the compound of the formula (I) is a compound of the formula (Id)

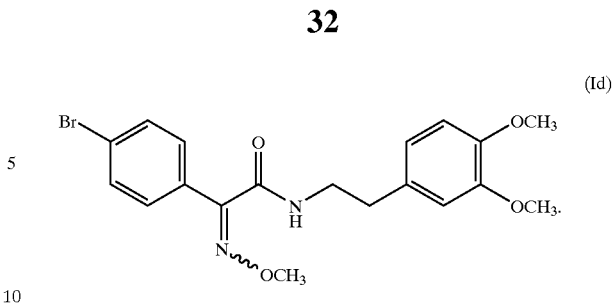
(Id)

6. An active compound combination according to claim 1 wherein the compound of the formula (I) is a compound of the formula (Ie)

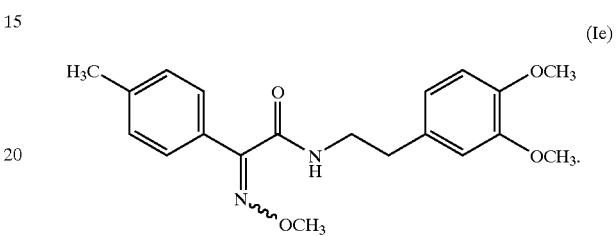
(Ie)

7. An active compound combination according to claim 1 wherein the compound of the formula (I) is a compound of the formula (If)

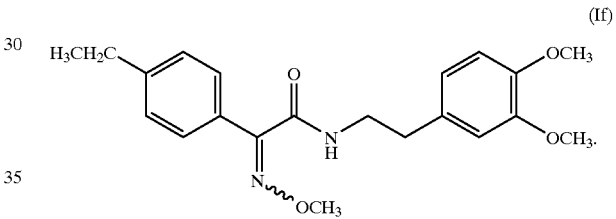
(If)

8. A method for controlling fungi comprising applying an active compound combination according to claim 1 to the fungi and/or the habitat of the fungi.

9. A process for preparing a fungicidal composition comprising mixing an active compound combination according to claim 1 with one or more extenders and/or surfactants.

* * * * *